United States Patent [19]

Eggers et al.

[11] Patent Number: 5,380,327
[45] Date of Patent: Jan. 10, 1995

[54] DEVICE FOR CONNECTING BONE FRAGMENTS BY MEANS OF A BONE PLATE

[75] Inventors: Christoph Eggers, Hamburg; Arnold Keller, Kayhude, both of Germany

[73] Assignee: Waldemar Link GmbH & Co., Hamburg, Germany

[21] Appl. No.: 160,056

[22] Filed: Dec. 1, 1993

[30] Foreign Application Priority Data

Dec. 4, 1992 [DE] Germany ............... 9216565[U]

[51] Int. Cl.⁶ ............................................. A61B 17/56
[52] U.S. Cl. .......................................... 606/69; 606/71
[58] Field of Search ............... 606/61, 60, 69, 53, 606/54, 59, 72, 70, 73, 71

[56] References Cited

U.S. PATENT DOCUMENTS

| | | |
|---|---|---|
| 2,251,209 | 7/1941 | Stader . |
| 4,135,505 | 1/1979 | Day . |
| 4,794,918 | 1/1989 | Wolter ................................. 606/72 |
| 4,887,596 | 12/1989 | Sherman ............................. 606/61 |
| 5,067,955 | 11/1991 | Cotrel ................................. 606/61 |
| 5,176,678 | 1/1993 | Tsou ................................... 606/61 |
| 5,282,863 | 2/1994 | Burton ............................... 606/61 |

FOREIGN PATENT DOCUMENTS

| | | |
|---|---|---|
| 0016270 | 10/1980 | European Pat. Off. . |
| 0242842 | 10/1987 | European Pat. Off. . |
| 0201024 | 8/1989 | European Pat. Off. . |
| 0392927 | 10/1990 | European Pat. Off. . |
| 0507162 | 10/1992 | European Pat. Off. . |
| 2499400 | 8/1982 | France . |
| 2718515 | 11/1977 | Germany . |
| 90/12547 | 11/1990 | WIPO . |

Primary Examiner—Tamara L. Graysay
Attorney, Agent, or Firm—Chilton, Alix & Van Kirk

[57] ABSTRACT

Device for connecting bone fragments by a bone plate (1), which is to be connected to the bone fragments using screws (5). A screw (5) or group of screws is connected to a coupling part (6) at a fixed angle, which coupling part surrounds the bone plate (1) transversely, on the one hand forming with the underside (3) of the plate a swivel bearing and on the other hand having a cover plate (10), which contains at least three fixing screws (16) arranged laterally offset with respect to the swivel bearing. By adjusting these fixing screws, the coupling part with the associated screws can be angularly adjusted with respect to the bone plate.

8 Claims, 1 Drawing Sheet

DEVICE FOR CONNECTING BONE FRAGMENTS BY MEANS OF A BONE PLATE

Bone plate arrangements are known, in particular for spinal surgery, which make it possible to effect a fixed angle relationship between a bone screw and a bone plate, for example in order to give a bone fragment or a vertebra a predetermined angular position in relation to adjacent fragments or vertebrae (EP-B 0 201 024, EP-A 0 242 842, WO-A 90/12547, EP-A 0 507 162, FR-A 24 99 400, DE-A 27 18 515, EP-A 392 927, U.S. Pat. No. 2,251,209, EP-A 16 270). The known arrangements are complicated in terms of use and/or unreliable in terms of the angular fixing and/or take up too much space.

According to the invention, these disadvantages are eliminated or attenuated by the inclusion of at least one coupling part for fixing a screw at a fixed angle with respect to the bone plate. The coupling part transversely surrounds the bone plate and forms a swivel bearing with the underside of the plate. The coupling part also includes a cover plate which contains at least three fixing screws arranged laterally offset with respect to the swivel bearing. More specifically, the coupling plate further includes a base plate that supports the swivel bearing and is rigidly connected to the cover plate via two side walls. One part of the swivel bearing may be formed by the head of the screw while another part is formed by at least one depression provided on the underside of the bone plate.

The invention is discussed in greater detail hereinbelow with reference to the drawing, which illustrates an advantageous exemplary embodiment and in which.

Figure 1:
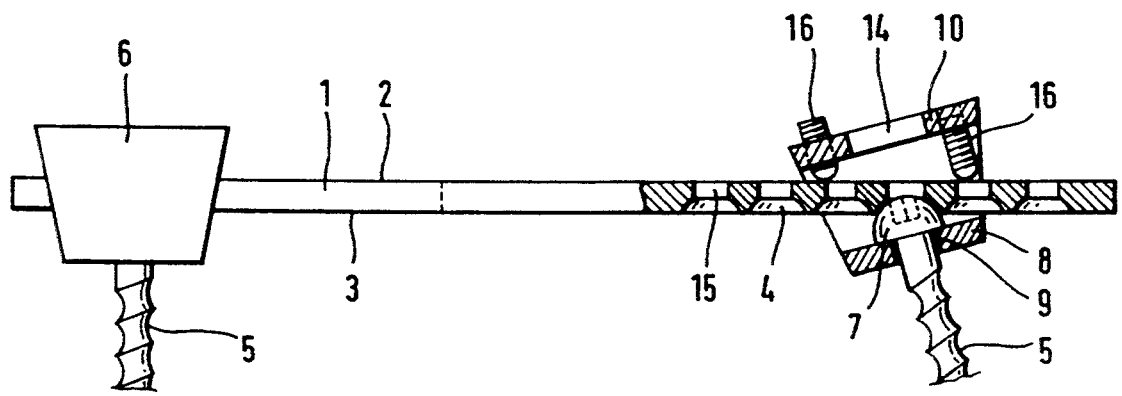
FIG. 1 shows a partially cutaway view of the longitudinal side.
Figure 2:
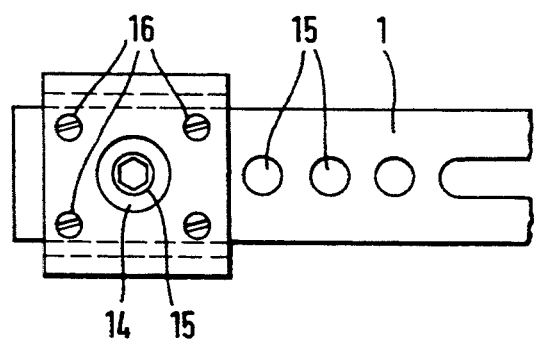
FIG. 2 shows a plan view of half of the device.
Figure 3:
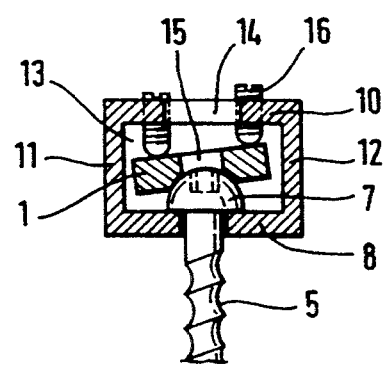
FIG. 3 shows a cross-section.

The rail-like bone plate 1 has a plane upper side 2. The underside 3 comprises, at least at each end, a series of centred, spherical depressions 4 and, if so desired, in the central area, an elongate hole which allows a further bone fragment or a vertebra or a plurality of fragments to be fixed between two bone fragments or vertebrae which are to be connected to the ends of the bone plate. The bone plate can, if so desired, be bent in a known manner in order to match a desired bone path. In general, however, this is not necessary, on account of the angular adjustability of the bone screws which is afforded according to the invention. If so desired, the bone plate can also exhibit any type of curvature from the outset.

For the purpose of connecting the bone plate to a bone fragment or vertebra, use is made of bone screws 5 which are connected to the bone plate by means of a coupling part 6. In this respect, the angle relationship between the bone screw 5 and the coupling part 6 is predetermined and unvariable. This can be achieved, for example, by means of the bone plate and the coupling part being joined to one another as one piece or by means of their interacting surfaces being adapted to one another in shape so that the predetermined angle relationship is obtained. The latter is the case in the example shown, where the plane underside of the screw head 7 is pressed onto the plane upper side of the base plate 8 of the coupling part 6. The shaft of the screw and the coupling part bore 9 receiving it can also be designed in such a way that they ensure the desired angle relationship. In the present case this angle relationship is characterized in that the axis of the bone screw 5 is perpendicular to the base plate 8 of the coupling part 6.

The coupling part 6 has a cover plate 10 which is parallel to the base plate 8 and is connected rigidly to the base plate via two side walls 11, 12. There is thus formed, between the cover plate, the base plate and the side walls, a channel 13 which is open at both ends and which receives the bone plate 1. The cover plate 10 comprises a bore 14, through which a screwdriver has access to the screw head 7. In the example shown, the bone plate 1 also has bores 15 in each case concentric to the depressions 4 on the underside, through which bores 15 a screwdriver has access to the screw head 7, so that the bone screw 5 can be turned even if the bone plate 1 is situated in the coupling part. However, this is not absolutely necessary since, in many cases, the bone screw 5 with the associated coupling part 6 can be screwed into the associated bone fragment before the bone plate 1 is introduced into the coupling part 6.

For the purpose of fixing the bone plate 1 in the coupling part 6, four headless screws are provided in the cover plate 10 of the coupling part 6, the axes of which headless screws 16 are approximately perpendicular to the plane of the cover plate 10 and they are also approximately perpendicular to the extension of the bone plate 1. They are situated to different sides, at a distance from the screw head 7, and in the corners of an imaginary rectangle, the sides of which are parallel or transverse to the extension direction of the bone plate. In addition, they are situated within the lateral limits of the bone plate 1 so that, when they are screwed into the coupling part, they eventually make contact with the upper side 2 of the bone plate, and do so at each practical angular setting of the bone plate relative to the coupling part. In geometrical terms, three screws would be sufficient, but it is difficult to square this figure with the design requirements.

This angular setting is variable because the bone plate is supported by the base plate 8 via a swivel bearing, which permits a swivel movement about the transverse axis and/or about the longitudinal axis of the bone plate. In the example shown, this swivel bearing is formed by means of a selected depression 4 on the underside of the bone plate in each case interacting with the surface of the screw head 7, which surface is of essentially spherical design in conformity with the depressions 4. The desired angular position of the bone plate relative to the coupling part is then set by means of the screws 16, which are screwed to a greater or lesser extent into the coupling part.

This arrangement affords an extraordinarily secure connection between the bone plate and the coupling part, since, on the one hand, the bone plate is locked with respect to the coupling part in the longitudinal direction and transverse direction by means of the depression 4 interacting with the screw head 7 and, on the other hand, the screws 16 determine the angular setting in a defined and unalterable manner. Since the bone plate bears on the screw head 7 relative to the force of the screws 16, this screw head 7 is pressed against the base plate 8 of the coupling part 6 and is therefore similarly secured.

The bone plate can also be used other than with the coupling parts according to the invention. For example, it can be screwed to a bone fragment directly at one end via the bores 15, while at the other end it interacts via a coupling part 6 with the bone fragment situated there. Nor is it necessary for the bone plate to have depressions 4 on the underside, since the lower edge of the bores 15 is also capable of forming a swivel bearing with the screw head 7. The underside of the bone plate can also be completely smooth (without depressions 4 and without bores 15), since in this case too a swivel bearing with the screw head 7 is obtained at any desired point on the lower surface. Nor is it necessary for the coupling-side part of the swivel bearing to be formed by the screw head 7; instead, any other suitable raised area can be provided for this purpose inside the coupling part, for example a conical point. The bone screw (or else a group of bone screws) could then be connected in another manner to the base plate of the coupling part. Finally, the cover plate 10 of the coupling part does not need to be rigidly connected to the base plate 8; instead, it can in this respect constitute a separate plate, which is connected to the base plate by means of a plurality of screws lying outside the lateral limits of the bone plate 1, which screws are screwed to differing extents into the base plate in order to give the bone plate 1, which is impinged upon over a large area by the cover plate 10, the desired angular setting with respect to the base plate 8.

We claim:

1. In a device for connecting bone fragments comprising a bone plate (1), at least one bone screw for connecting the bone plate to the bone fragments and at least one coupling part (6) for fixing the screw at a fixed angle with respect to the bone plate (1), characterized in that the coupling part (6) transversely surrounds the bone plate and is positioned at a fixed angle to the screw, said screw forming a swivel bearing with the plate, said coupling part having a cover plate (10) carrying at least three fixing screws (16) arranged laterally offset with respect to the swivel bearing.

2. Device according to claim 1, characterized in that the coupling part includes a base plate (8) supporting the swivel bearing, the cover plate and the base plate being connected rigidly to one another, and the fixing screws (16) acting on the upper side (2) of the bone plate (1).

3. Device according to claim 2, characterized in that said a least one bone screw has a head and a shaft with one part of the swivel bearing being formed by the head (7) of said bone screw (5), the base plate (8) being provided with a receiving bore (9) for receiving the shaft of the bone screw.

4. Device according to claim 2, characterized in that at least one depression (4) for forming one part of the swivel bearing part is provided on the underside (3) of the bone plate (1).

5. Device according to claim 4, characterized in that said a least one bone screw has a head forming another part of the swivel bearing and at least one of the two swivel bearing parts is of spherical design.

6. Device according to claim 4, characterized in that the bone plate (1) has a tool opening (15) at the site of the depression (4).

7. Device according to claim 2, characterized in that the cover plate (10) is connected rigidly to the base plate (8) via two walls (11, 12) surrounding the bone plate (1).

8. Device according to claim 1, characterized in that four fixing screws (16) are provided, connecting lines between the screws extending parallel and transverse to the direction of the bone plate (1).

* * * * *